US009375194B2

(12) United States Patent
Kwiat

(10) Patent No.: US 9,375,194 B2
(45) Date of Patent: Jun. 28, 2016

(54) REAL-TIME LOCALIZATION OF AN INTERVENTIONAL TOOL

(71) Applicant: Doron Kwiat, Tel Aviv (IL)

(72) Inventor: Doron Kwiat, Tel Aviv (IL)

(*) Notice: Subject to any disclaimer, the term of this patent is extended or adjusted under 35 U.S.C. 154(b) by 111 days.

(21) Appl. No.: 13/785,130

(22) Filed: Mar. 5, 2013

(65) Prior Publication Data
US 2013/0317347 A1 Nov. 28, 2013

Related U.S. Application Data

(60) Provisional application No. 61/652,283, filed on May 28, 2012, provisional application No. 61/675,957, filed on Jul. 26, 2012.

(51) Int. Cl.
| A61B 5/00 | (2006.01) |
| A61B 8/08 | (2006.01) |
| A61B 5/055 | (2006.01) |
| A61B 5/06 | (2006.01) |
| A61B 8/00 | (2006.01) |
| A61B 6/03 | (2006.01) |
| A61B 6/12 | (2006.01) |
| A61B 6/00 | (2006.01) |

(52) U.S. Cl.
CPC .............. *A61B 8/0841* (2013.01); *A61B 5/0026* (2013.01); *A61B 5/055* (2013.01); *A61B 5/062* (2013.01); *A61B 8/463* (2013.01); *A61B 8/523* (2013.01); *A61B 8/5223* (2013.01); *A61B 5/064* (2013.01); *A61B 6/032* (2013.01); *A61B 6/12* (2013.01); *A61B 6/463* (2013.01); *A61B 2034/2063* (2016.02); *A61B 2034/2072* (2016.02)

(58) Field of Classification Search
CPC ............... A61B 19/5244; A61B 2019/5263; A61B 2019/5272; A61B 2019/5289; A61B 2019/5454; A61B 2019/5466; A61B 5/0026; A61B 5/055; A61B 5/062; A61B 5/064; A61B 6/032; A61B 6/12; A61B 6/463; A61B 8/0841; A61B 8/463; A61B 8/5223; A61B 8/523
See application file for complete search history.

(56) References Cited

U.S. PATENT DOCUMENTS 6,314,310 B1 * 11/2001 Ben-Haim et al. ............ 600/424
8,565,860 B2 * 10/2013 Kimchy et al. ............... 600/436

* cited by examiner

*Primary Examiner* — Ruth S Smith
(74) *Attorney, Agent, or Firm* — Browdy and Neimark, PLLC

(57) ABSTRACT

A traceable surgical tool is positioned, monitored and displayed in real-time directly with pre-scanned three dimensional CT/MRI slices of a patient. The tool positioning and inclination is obtained by real time combined ultrasound (US)/RF transmissions between at least four transmitting units (TUs) and a mobile unit (MU) attached to or included in the tool. No more than three of the TUs may be coplanar. In some embodiments, at least one TU includes two US transmitters transmitting at different frequencies. Image space coordinates of the CT/MRI scanned patient are mapped by a one-to-one transformation onto real space coordinates of the patient undergoing a surgical procedure. The mapping is aided by, in the real space environment, touching once each of at least three markers fixedly attached to the patient and pre-scanned with the patient in the image space. A high resolution location of the tool is recorded in real-time, and the tool's position is displayed together with reconstructed CT/MRI slices in real time.

18 Claims, 13 Drawing Sheets (A)  (B)

REAL-TIME LOCALIZATION OF AN INTERVENTIONAL TOOL

CROSS REFERENCE TO RELATED APPLICATIONS

This application is related to and claims priority from U.S. Provisional Patent Applications No. 61/652,283 titled "Real-time stereotactic traceable interventional tool with MRI/CT" and filed May 28, 2012, and No. 61/675,957 titled "Method and device for real-time tracing and localization of interventional tool using ultrasound and RF time-stamping" and filed Jul. 26, 2012, both of which are incorporated herein by reference in their entirety

FIELD

Embodiments disclosed herein relate in general to stereotactic monitoring and positioning of a first object relative to a second object, and in particular to real time stereotactic monitoring and positioning of a interventional tool in a medical procedure, using pre-scanned MRI/CT slices and real-time combined ultrasound (US)/radio frequency (RF) transmissions.

BACKGROUND

Navigation systems for tracking and navigating an instrument in space are known. Such systems may be based on electromagnetic, optical, acoustic and other physical principles. For example, a navigation system can be used to track an instrument during an interventional medical procedure on a patient. Such tracking can determine the instrument's position relative to a target organ without physically viewing the instrument. The tracking may include direct tracking of a particular instrument section external to the patient or tracking of a distal point of the instrument within the patient. In an example, the external section is a proximal end of a long and substantially rigid instrument, while the distal point is a distal instrument end or "tip".

Tracking of the 3D position and spatial inclination of an instrument through combined ultrasound (US) time of flight (TOF) and time-stamping is also known. US TOF based positioning methods require accurate synchronization between a transmitter and a receiver to compensate for respective clock inaccuracies and drift. The synchronization uses RF transmissions. Such methods suffer from several problems. 1) the RF propagation is assumed instantaneous and thus delay errors are introduced and affect readings of TOF; 2) the use of a small number of transmitters involves line-of-sight (LOS) problems caused by obstructing objects which prevent signals from arriving at receivers; 3) while LOS obstruction may be overcome by fast sequential or simultaneous scanning over a large number of transmitters, this procedure slows the acquisition and the positioning algorithms and therefore is inadequate for tracking fast moving instruments or random hand movements of e.g. physicians in an operating room. Also, the synchronization of receiver and transmitter clocks requires initial calibration. If the RF propagation is not assumed to be of infinite speed, long sampling windows introduce ambiguities caused by reflected US waves, and 3D triangulation requires special attention to positioning of at least four transmitters in order to avoid singularities.

The guiding of an interventional tool during operation within the body is important. Conventional procedures are conducted using X-ray and/or US imaging technology to facilitate tool guidance. Typical image guided navigation systems (e.g. as described in U.S. Pat. No. 8,359,730) require dynamic reference frames to track the position of the patient. The dynamic reference frame is generally affixed to the patient in a permanent or immovable fashion. The dynamic reference frame may be used as a fiducial marker and may, therefore, be attached to the patient during the acquisition of pre-operative images. However, such markers on the body are connected to a measurement and registration unit by wires. Use of wireless transmission is problematic, since wireless-enabled markers would need transmitters that cannot be placed inside an MRI scanner. Therefore, both patient and attached markers must be fixed to the operation bed, since the reference point is set with respect to the bed.

There is therefore a need for, and it would be advantageous to have methods and systems for real time navigation and guiding of a moving instrument relative to a stationary object that do not suffer from the abovementioned problems and disadvantages

SUMMARY

Embodiments disclosed herein relate to a system and method for precise 3D real-time positioning (localization) of a randomly moving object (e.g. an instrument) relative to a stationary reference point. The system and method enable tracking and monitoring in real time of the position and spatial inclination of the moving object through combined use of US and RF transmissions and pre-acquired MRI/CT scan data. The MRI/CT data is acquired in an "image space". The system and method are particularly useful in medical applications, such as localization of an interventional tool (as moving object) used during an interventional procedure in an operating room (considered to be a "real space"). The interventional tool may e.g. a scalpel or biopsy tool having a tip, while the stationary object would be a patient or a particular organ of a patient. The tool may be used by an operator (e.g. interventional radiologist or surgeon) in combination with image "slices" reconstructed from a pre-scanned MRI/CT 3D data volume of the organ to operate on a "target lesion" of the organ. Different MRI/CT slices may be reconstructed and displayed together with the tool in real time: a "current" slice where the tool's tip is currently located, a "target" slice showing the target lesion, both slices being reconstructed in real time and orthogonal to the tool's tip, and a "saggital" slice saggital to the axis line drawn between the tool tip and the lesion target. The saggital slice can be chosen at any desired rotation angle around the axis and can help the operator in planning a direct propagation path through the organ to the target. The operator can view markings of the tip position, lesion position and marker positions in real-time or on demand on a monitor (e.g. a video screen). The operator may thus proceed to operate on the patient while viewing the tool and pre-acquired imagery of the organ/lesion on the screen.

In an embodiment, a system disclosed herein comprises at least four stationary transmitting units ("TU"s), each TU including a US transmitter, a RF transmitter, a local processing unit (e.g. a digital signal processor or "DSP") and a TU clock. The TUs must be arranged in space such that no more than three TUs are coplanar. The system further comprises a mobile unit ("MU") which includes at least two US receivers, an RF receiver, a MU clock and a local processing unit (e.g. a DSP). The TU and MU clocks record times of both US and RF transmission and reception. The RF transmitters and receivers are configured for transmitting and receiving data that includes time-stamp data (or "RF CLOCK DATA"), identification data, control data and other data if necessary. In particular, RF time-stamp data may be transmitted in parallel with US pulse transmissions from the same TU, such that upon the start of transmission of the US pulse, the TU clock is read and its count is sent as RF CLOCK DATA. The system further comprises a central control unit (CCU), implementable for example in a personal computer (PC). The CCU is configured to perform various control and data processing functions related to all components and functionalities of the system. The CCU communicates with the MU and the TUs, using for example RF communications. RF transmissions from a MU to the CCU may include information such as TOF and position. RF transmissions from a TU to the CCU may include initialization and control instructions. CCU transmissions to the MU and TUs may include initialization and control instructions and other data. The MU processing unit processes received signals (and associated data such as ID and/or time of receipt of the signal) and, using US TOF, calculates coordinates of the MU position relative to each of the TUs, and accordingly relative to a reference point (e.g. a corner of the operating room). The MU then updates the CCU with its present location. The CCU is configured to continuously receive, in real-time, the location data from the MU and to provide this information for display in real time.

In an embodiment, each TU US transmitter is configured to transmit time modulated signals on a given frequency or frequency bands. Alternatively, a TU may include two US transmitters that transmit on two different frequencies f1 and f2. Each MU US receiver can receive transmissions from one or more US transmitters on respective frequencies. This provides data compactness and an increase in the US pulse rate, since one can send a much larger number of ultrasonic pulses during a transmission window and thus increase accuracy. The increased accuracy may be obtained in a variety of ways: by averaging over a larger number of US pulses, by reducing ambiguities caused by reflections, or by reducing error due to instabilities in RF detection in the receiver, estimated at 10 μsec (≈3.4 mm) The combination of RF TOF and RF CLOCK DATA removes the need for initial calibration of the RF transmitter and receiver clocks, yet adds a need for corrections due to RF detection delays due to fluctuations and instabilities of receiver/transmitter circuits. The use of US pulses with different frequencies allows reduction in total sampling time. It also allows synchronization of US transmitter and receiver clocks through comparison of relative amplitudes of received signals without physically measuring distance between the receivers and transmitters for initial synchronization.

A one-to-one coordinate mapping from the "image space" to the "real space" is aided by use of at least three markers fixedly attached to the patient. The markers are MRI/CT scanned together with the organ and provide a frame of reference in both coordinate systems. When the patient is transferred to the operating room environment, each marker is touched by the tool once, to register its position in the real space coordinate system. The image space can be one-to-one mapped to the real space by reading each marker's position in the real space coordinate system and through knowledge of each marker's position in the image space (e.g. MRI/CT) coordinate system. The marker touching procedure also allows for tracking the position of the markers in case of slight movements of the patient/organ, thus enabling to correct for motion related distortions. LOS hindrances may be overcome by reading the TOF from all stationary TUs to the MU receivers at a fast rate and by using the lower limit of US frequencies (<100 kHz), thereby providing a larger cone of propagation of ultrasonic waves.

In an embodiment there is provided a system for stereotactic positioning in real time of a first object relative to a second object, the first object having a tip, the system comprising: at least four TUs arranged spatially such that no more than three TUs are coplanar, each TU including at least one US transmitter, a RF transmitter and a TU clock, wherein at least one TU includes two US transmitters that transmit on two different frequencies f1 and f2; a mobile unit (MU) fixedly coupled to the first object, the MU including a MU clock, a RF transmitter/receiver and two US receivers spaced apart and positioned in a predetermined geometrical relation relative to the first object tip, wherein one receiver is adapted to receive US transmissions on frequency f1 and wherein the other receiver is adapted to receive US transmissions on frequency f2; and a central processing unit configured to determine a real space position of the first object tip based on US TOF data obtained from US transmissions between each TU US transmitter and each MU US receiver and to display simultaneously the real space tip position together with reconstructed image space data of the second object on a display.

In an embodiment there is provided a method for stereotactic positioning in real time of a first object relative to a second object, the first object having a tip, the method comprising the steps of: providing at least four TUs arranged spatially such that no more than 3 TUs are coplanar, each TU including at least one US transmitter, a RF transmitter capable of transmitting time-stamp data and a TU clock, wherein at least one TU includes two US transmitters that transmit on two different frequencies f1 and f2; providing a mobile unit (MU) fixedly coupled to the first object, the MU including a MU clock, a RF transmitter/receiver and at least two US receivers spaced apart and positioned in a predetermined geometrical relation relative to the first object tip, wherein one receiver is adapted to receive US transmissions on frequency f1 and wherein the other receiver is adapted to receive US transmissions on frequency f2; acquiring a 3D data volume of the second object in an image space; determining a real space position of the first object tip based on US TOF data obtained from combined RF and US transmissions between each US transmitter and each US receiver; and displaying simultaneously the real space tip position together with images of the second object reconstructed from the 3D image space data volume, thereby allowing the real time stereotactic positioning of the first object relative to the second object.

BRIEF DESCRIPTION OF THE DRAWINGS

Non-limiting examples of embodiments disclosed herein are described below with reference to figures attached hereto that are listed following this paragraph. The drawings and descriptions are meant to illuminate and clarify embodiments disclosed herein, and should not be considered limiting in any way.

DETAILED DESCRIPTION

Figure 1A:
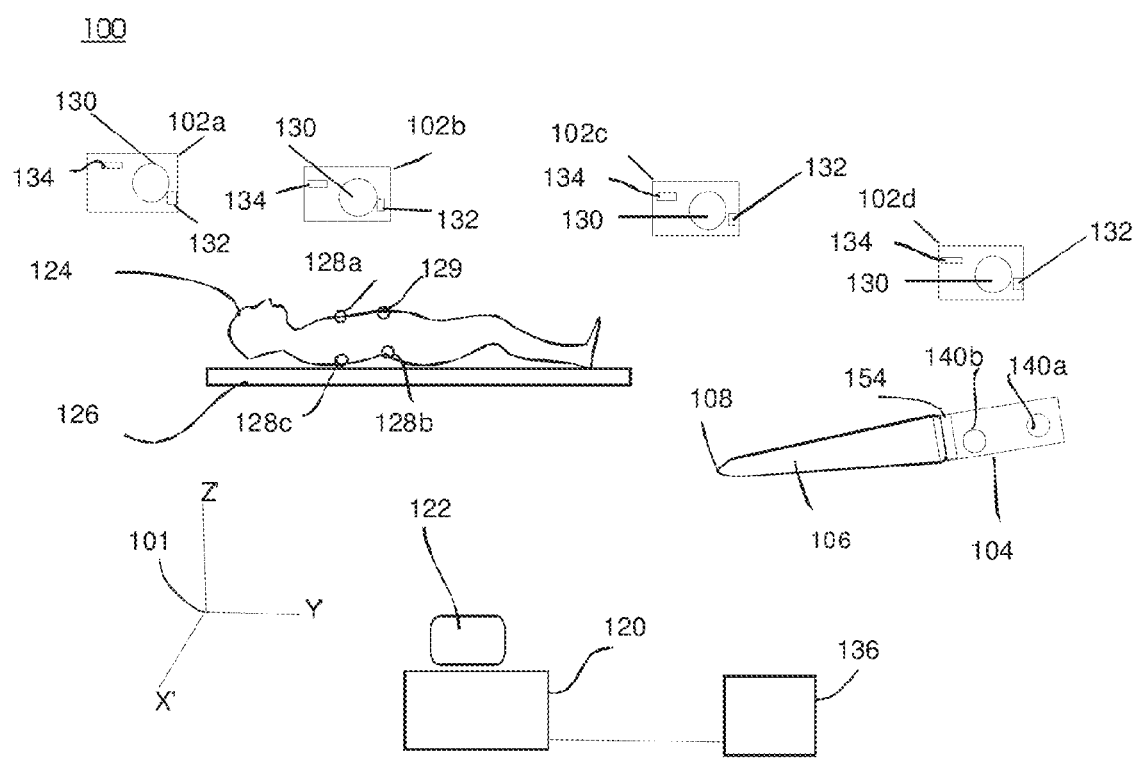
FIG. 1A shows a general view of a system disclosed herein.
Figure 1B:
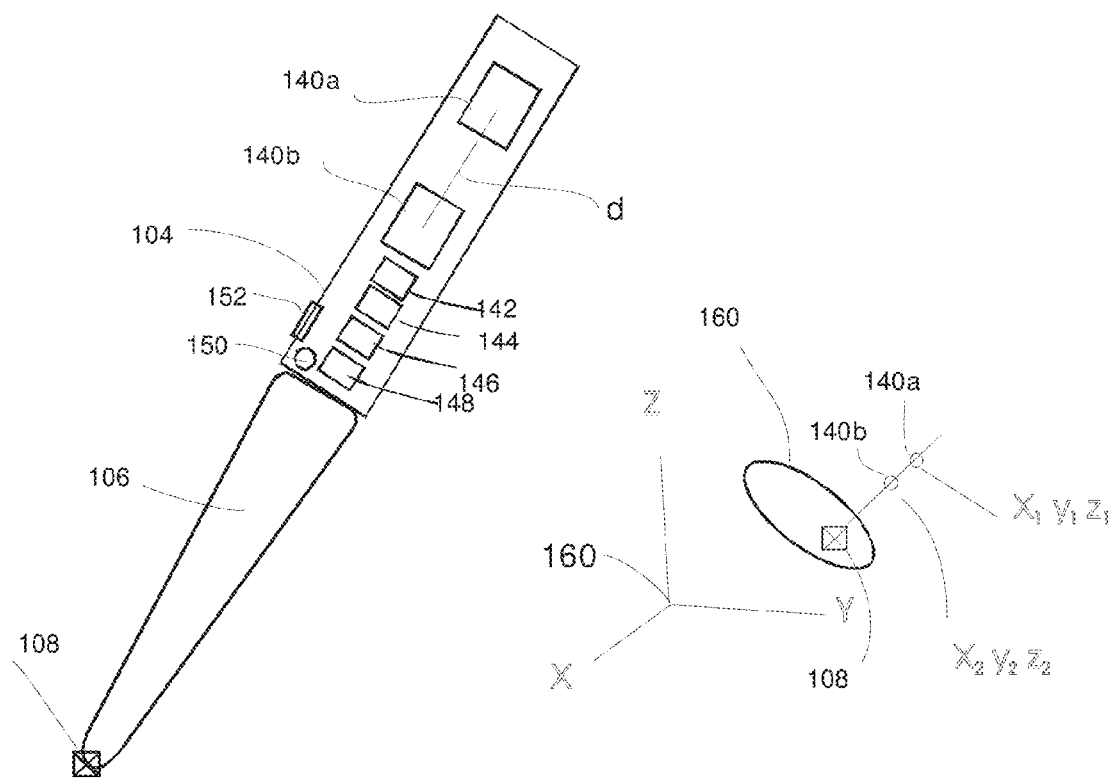
FIG. 1B shows an enlargement of a tool disclosed herein and its position and inclination in a real space coordinate system.

FIG. 1A shows a general view of a system for stereotactic tracking of a first moving object relative to a second, stationary object disclosed herein and marked 100. The system is described exemplarily with reference to an operating room environment, with the first object being an interventional tool and the second object being an organ of a patient. System 100 comprises at least four transmitting units (TUs) 102a-d, positioned at different locations (e.g. at or near corners of the room) with respect to a reference point (coordinates origin) 101 in the room. TUs 102 must not all be located in the same plane (i.e. must not all be co-planar). Each TU includes a US transmitter 130, a RF transmitter 132 and a clock 134. A US transmitter may transmit on one or several different frequencies. In an embodiment, all TUs are supplied from a central power supply (not shown) and connected to each other by a line supply (not shown). Optionally, each TU may include an independent power source (not shown). System 100 further comprises a mobile unit (MU) 104 included in, or attached to a tool 106 having a tool tip 108. An enlargement of the MU+tool and its position and inclination in a real space coordinate system X-Y-Z is shown in FIG. 1B. MU 104 includes at least two US receivers 140a and 140b, a RF receiver 142 and a RF transmitter 144. US receivers 140a and 140b are placed apart at a fixed given distance "d", and at known geometrical positions with respect to tip 108. MU 104 further includes a local processing unit (e.g. a DSP) 146 for processing signals and associated data such as ID data enabling to distinguish between different signals and time-stamp data. MU 104 further includes a clock 148, a power supply (e.g. battery) 150, an optional "start" button 152 to start and stop data transmissions, an optional "connect to" adaptor 154 (FIG. 1A) for easy coupling of the MU to various operation handles (e.g. tools or instruments), and electronics for filtering amplification and detection (not shown). DSP 146 includes a memory (not shown). MU 104 receives RF and US signals transmitted by TUs 102. System 100 further comprises a central control unit (CCU) 120 configured to perform various control and data processing functions related to all components and functionalities of the system. In particular, CCU 120 is configured to receive continuously, in real-time, location data from the MU and to present this information on a display 122. It is also configured to image process scanned 3D volumes and reconstruct image slices as desired. FIG. 1B also shows schematically a target organ 160 of the patient, tip 108 of the tool and the two MU receivers 140a and 140b. By reading the 3D positions of the two receivers, one can determine in 3D both the tool's tip position and the inclination of the tool relative to the target organ.

In the exemplary application environment illustrated in FIG. 1A, the tool is used to perform a medical procedure on a patient 124 shown schematically lying on an operating table 126. The patient has attached to his body at least three markers 128a, b, c. A fourth marker 129 may be added to allow motion tracking or to increase accuracy. The markers are positioned generally around a body section of interest and are used in a known way as a frame of reference in MRI/CT scans.

Each TU is adapted to transmit, and the MU is adapted to receive US signals and RF data and clock signals. Each US receiver may receive transmissions from all US transmitters on respective frequencies. The frequencies may be different for different TUs. The US and RF signals may be generated and transmitted simultaneously. Alternatively, the US and RF signals may be generated and transmitted sequentially. A CLOCK is registered upon US transmission and is carried by RF as CLOCK DATA to a receiver. Alternatively, in case the RF transmission carries CLOCK DATA, it may be sent later than a US transmission, as it will arrive at the receiver much faster than the US transmission. Alternatively yet, the TOF of RF transmissions may be assumed as instantaneous relative to that of US transmissions, and a RF transmission may serve just as a trigger to a CLOCK reading at a receiver. TUs transmitting on the same frequency are operated sequentially, at a large enough separation interval so as to prevent US signals from different TUs to arrive simultaneously at a receiver. The speed of the system may be increased by simultaneous transmission by different TUs using different US frequencies.

The MU is adapted to process the data received from a TU and, using TOF, to calculate in real time its (and the tool's) current coordinates relative to each of the TUs and accordingly relative to the reference point. With two receivers in a MU, the MU is also adapted to provide 3D inclination of the tool attached thereto.

In an embodiment, all clocks can count up to 12 bits temporal resolution and are precise and accurate to less than few nanoseconds drift per day. The clocks are used for synchronization between a MU US receiver and a particular TU US transmitter, by RF carrying TU CLOCK DATA with TU ID and transmission time-stamps. This allows to uniquely identify each transmitted RF signal with a particular TU transmitter. The TOF of a US pulse from a particular TU US transmitter to a particular MU US receiver is obtained as follows: the particular TU clock and the MU receiver clock are first synchronized using RF pulses. The MU clock is then triggered at the start of the US pulse transmission and stopped upon arrival of the US pulse from the particular TU. In addition, upon request, a data carrying RF pulse may be transmitted from a RF transmitter with respective TU CLOCK DATA at the start of the US pulse transmission. The TU CLOCK DATA is read at the RF receiver. The two clocks can be synchronized by triggering the MU clock upon arrival of a transmitted US pulse, reading the difference in the two clocks and measuring the distance between transmitter and receiver. Hence, a TOF will suffice for determining the distance between transmitter and receiver. This method allows for a more accurate determination of US TOF by reducing RF delayed detection errors. Thus, usually, RF pulses will be used only to trigger the clock at the receiver. However, once in a while, data carrying RF synchronization will be introduced to correct biased readings due to antenna delays (e.g. temperature related).

Figure 2:
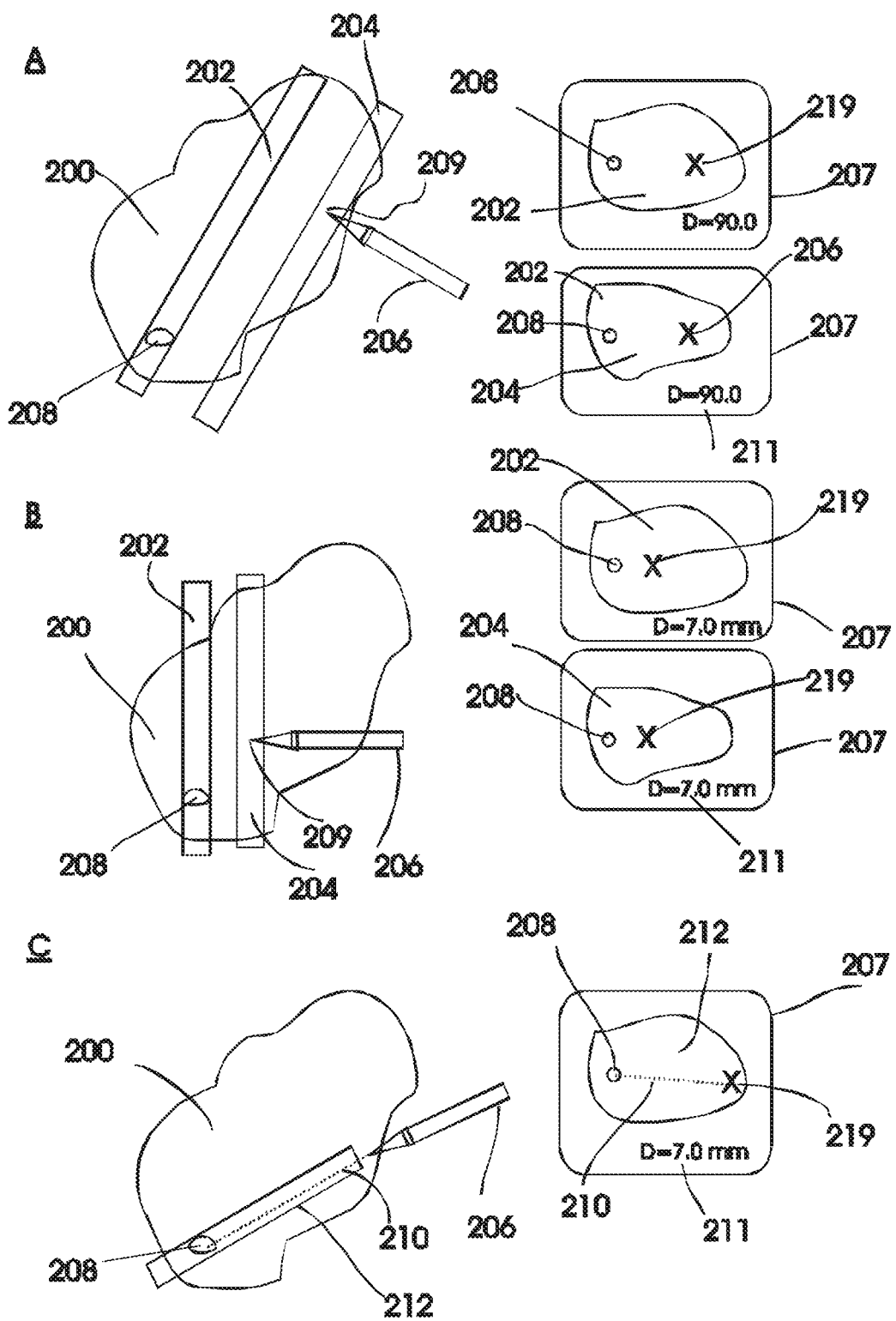
FIG. 2A shows schematically a tool orthogonal with respect to slices of a target organ in one position.
FIG. 2B shows the same as FIG. 2A but with the tool moved to another position.
FIG. 2C shows a saggital slice orthogonal to an axis drawn between the tool and the target organ.

FIGS. 2A-C show schematically exemplary display views of tool 206 with a tip 209 positioned relative to reconstructed MRI/CT slices of a target organ 200. FIG. 2A shows two parallel reconstructed slices 202 and 204. Slice 202 is a "target" or "lesion" slice through a lesion 208 and slice 204 is a "current" slice through a current tip position. Both slices are orthogonal to tool 206. The slices are displayed on a screen 207. A distance marked 211 between the current tip position and lesion 208 is also shown. FIG. 2B shows the tool moved to another position and inclination. FIG. 2C shows a "saggital" slice 212, which is saggital to a virtual axis 210 drawn between tool 206 and lesion 208. Slice 212 can be rotated at will around axis 210. The tool tip is marked on the display by an "x" and numbered 219.

Example of Use in an Interventional Procedure

Figure 3:
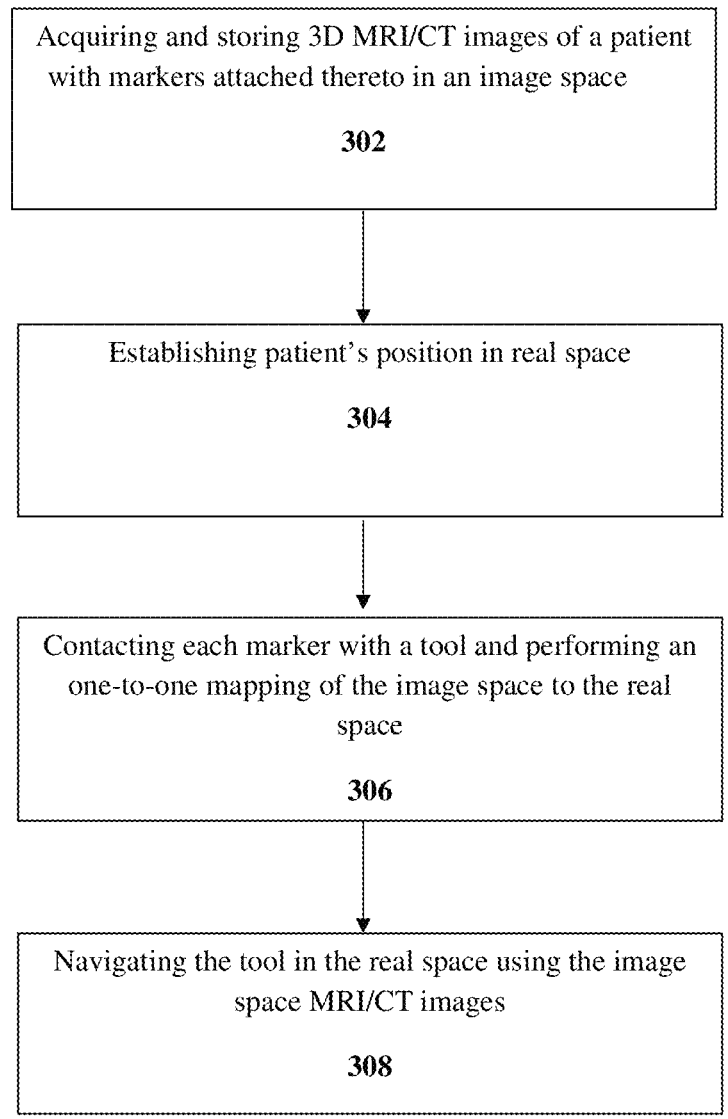
FIG. 3 shows schematically in a flow chart the use of system disclosed herein in a surgical interventional procedure.
Figure 5:
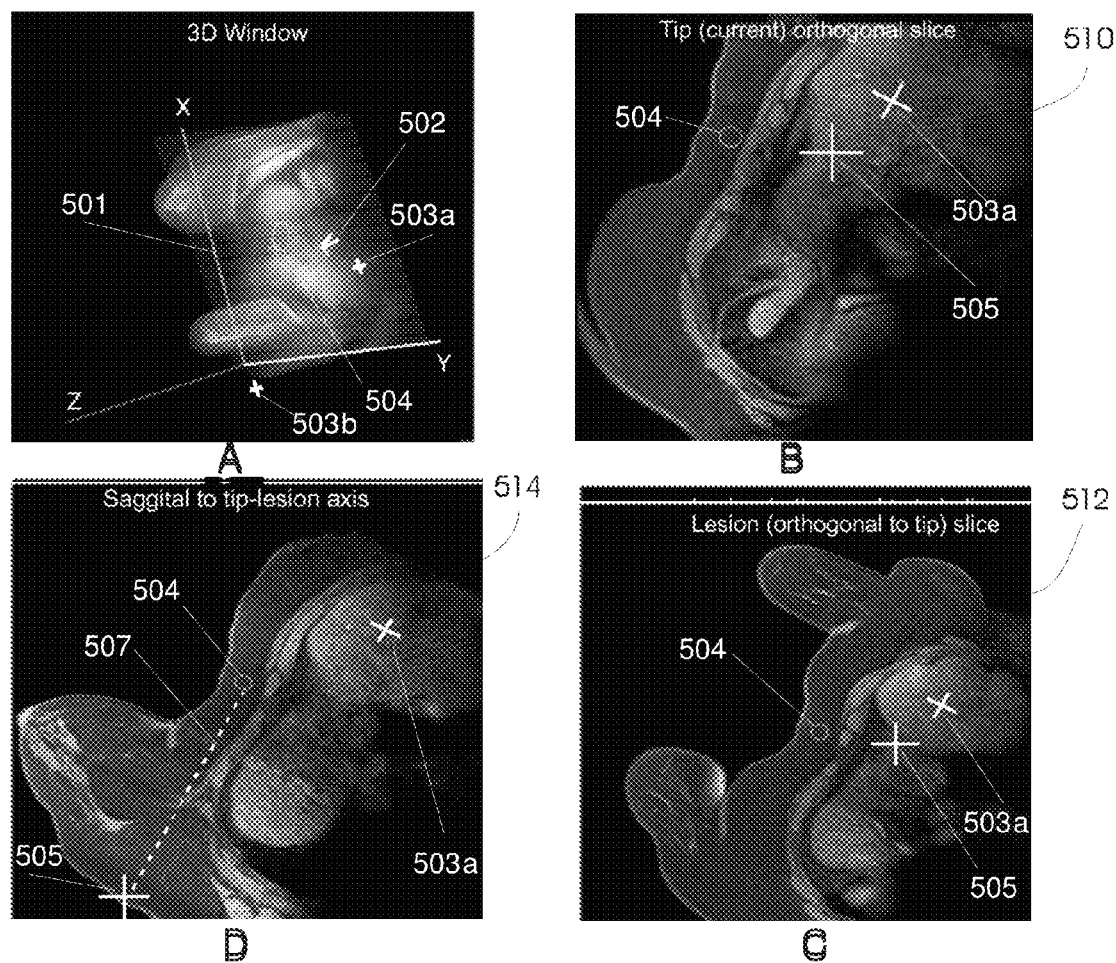
FIG. 5 shows actual experimental display views showing the tool with respect to slices of a target organ.

FIG. 3 shows schematically in a flow chart the use of system disclosed herein in an interventional surgical procedure. In step 302, 3D MRI/CT images of the patient and attached markers are pre-acquired and stored in an "image space". This procedure is performed normally in a separate location and not in the operating room. In step 304, the patient is transferred to an operating room (which represents the "real" or "operating" space), is laid down on an operating table, and has his/her true position established in the real space. The latter includes physically touching each marker with the tool tip and performing a transformation from the image space coordinate system to the real space coordinate system, as shown in FIG. 5. This allows a precise matching between the image space coordinate system and the patient's true position on the operating table. The real space position is displayed together with the tool tip and with pre-acquired MRI/CT image "slices" representing the "transformed position" of the patient/organ, allowing an operator to, in step 308, navigate the tool in real time using the high resolution information of the MRI/CT images. In an embodiment in which the tool includes or is attached to a MU with two receivers, tool inclination/orientation as well as position are provided. This allows display of a first (current) MRI/CT slice orthogonal to the tool axis and passing through the tool tip and of a second (target) MRI/CT slice orthogonal to the tool axis and passing through the target lesion, as shown schematically in FIGS. 2A, B. Additionally, this allows one to determine the distance between the tool's tip and the target lesion. Further, this allows display of a third (saggital) MRI/CT slice (FIG. 2C), and therefore allows the operator to watch simultaneously the current tool position and the target position in real-time. The whole process is performed fast enough so that statistical averaging of the signals by a large number of repetitions (NREP) can be achieved within a short enough period of time. This allows recording the position of the moving MU before it moves over more than a predetermined distance.

Figure 4:
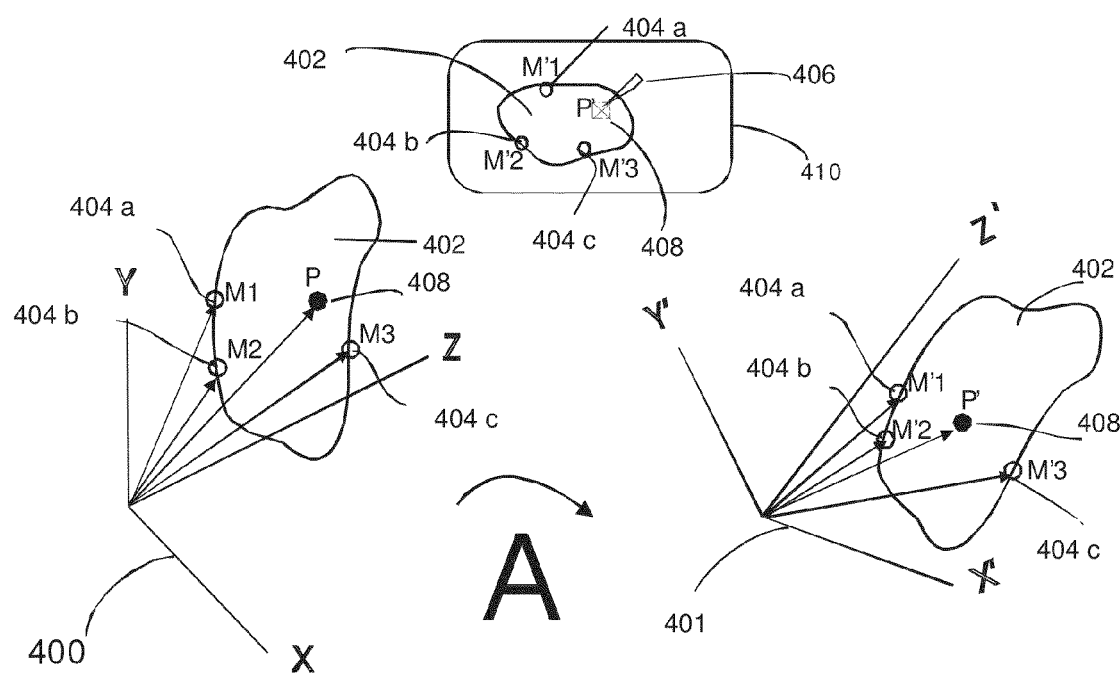
FIG. 4 shows schematically the 1:1 mapping from the image space coordinate system to the real space (operating table) coordinate system.

FIG. 4 shows schematically the 1:1 mapping from the image space coordinate system 400 to the real space (operating table) coordinate system 402. The figure shows a patient body 404 having three markers 404a, b, c fixedly attached thereto as well as a tool 406. The X-Y-Z coordinate system 400 represents the (scanning environment) image space and shows the markers as M1, M2 and M3. The X'-Y'-Z' coordinate system 402 represents the real space. The same markers are now marked as M'1, M'2 and M'3. A specific "target" organ" point P is indicated by 408 in both coordinate systems.

FIG. 5 shows actual experimental display views of a tool with respect to slices of a target organ: (A) shows a 3D volume view with markers 503a,b,c and lesions 504 and with a real time tool position and inclination 502 in image space coordinates X Y Z; (B) shows a current slice 510 orthogonal to the tool and touching a tool tip 505. Also shown encircled is the position of lesion 504; (C) shows a target lesion slice 512 orthogonal to the tool; and (D) shows a saggital slice 514 saggital to an axis 507 connecting the tool tip to the lesion. Also displayed is the calculated real-time distance "1" between the current position of the tool's tip and the target lesion.

RF Initialization and US TOF Determination

Figure 6:
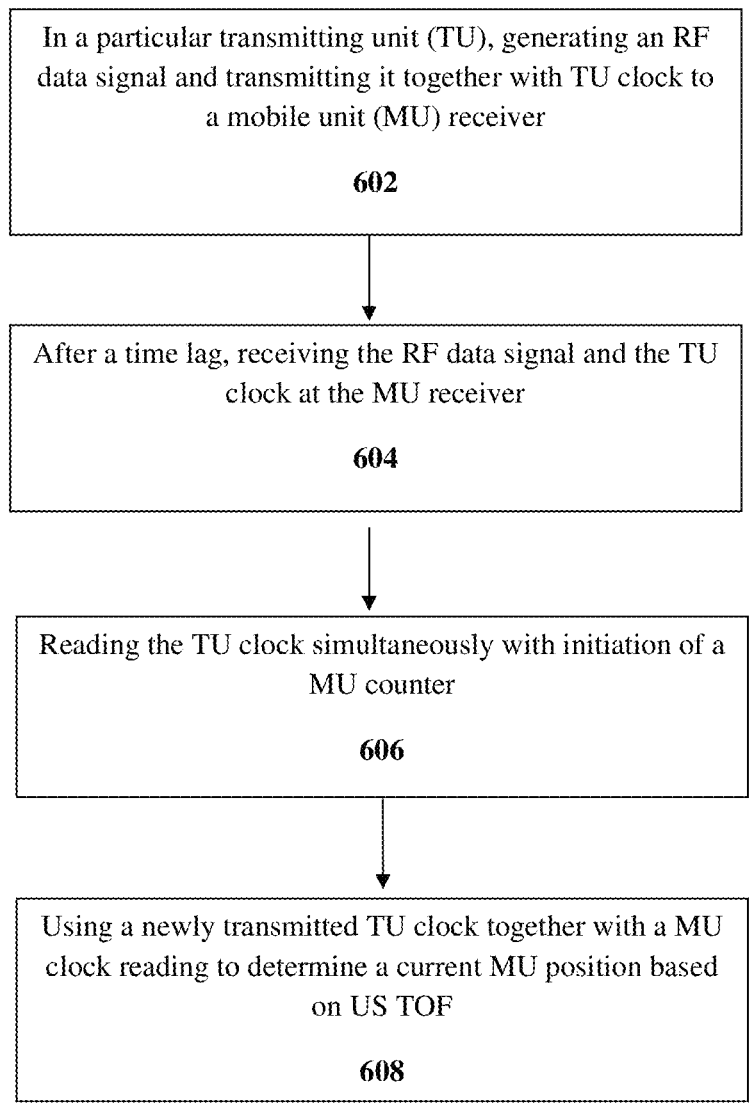
FIG. 6 schematically in a flow chart the initialization and TOF determination procedure.

In a first procedure, the determination of the ultrasound TOF from a particular TU US transmitter to a particular MU US receiver is performed as described in FIG. 6: In step 602, a RF DATA signal is initiated at the particular TU and transmitted with a simultaneously generated TU CLOCK reading to the particular MU. In step 604, the transmitted RF DATA+ TU CLOCK are received at the MU RF receiver with a certain time lag that is a function of the distance between the respective RF transmitters and receivers and the EM wave propagation speed. In step 606, the TU CLOCK is read simultaneously with initiation of a counter in the MU clock. Since the counting rates (CR) of both TU and MU clocks are known and fixed (except for negligible drift errors), the actual "initial" relative time difference between the RF signal transmission and reception (and respective TU and MU clocks) can be calculated, provided that the exact distance between the particular TU and MU is known beforehand. Steps 602-606 represent an "initialization" procedure. Once this "initial" time difference between the two clocks is calculated, the MU may be positioned randomly at a new "current" position, and without knowledge of this position, a "current" ultrasound TOF can be easily determined based on a current reading of a transmitted TU CLOCK and of the MU clock. The current position of the MU is then determined from the current US TOF reading and displayed in step 608. Four such TOF readings (between the MU and four TU US transmitters) are needed. The initialization procedure is repeated over all TUs with respect to a particular MU, and thereafter, the accurate distance between each TU to the MU can be calculated based on independent TOF measurements, without a-priori knowledge of the MU position. The required calculations are performed in the local MU processing unit. The initialization of the RF transmission is controlled and processed by the local TU processing unit.

In an alternative, second procedure, a RF signal is generated in a particular TU, transmitted simultaneously with a US pulse to the MU and used to start a MU receiver clock (initiate a MU counter). Upon (later) arrival at the MU of the US pulse and its detection, the MU clock is stopped to determine the US TOF. This procedure is repeated over all TUs and the TOF readings of at least four TUs are used to determine the current MU position and inclination. In some embodiments, the two procedures may be "interleaved", i.e. used alternately.

Error Handling

The TOF determination and MU positioning procedures may have deterministic, stochastic and motion errors. Deterministic errors may include internal delay errors in the electronics, which may cause a delay between the actual readings of the clocks and true counts, or errors due to group propagation of the transmitted RF signals and delays between a true arrival time of a signal at the receiver and the set point of detection. These delays can be considered almost fixed per given system and a given location, and therefore can be measured and accounted for by offsetting them in the MU processor.

Stochastic errors may be caused by thermal noise in the electronics, external noise introduced into air by reflections of RF signals, cable noise, air turbulences, etc. These errors may be assumed to be of the order of several nanoseconds, and can be reduced by an averaging procedure. Stochastic and clock errors can be reduced by taking a large number of clock readings and averaging them in the initialization stage. Each time a RF signal arrives at the receiving MU, the MU records the DATA from the specific TU and compares it to its own local clock. Thus, the relative time that the signal took to arrive from the TU to the receiving MU is available, without the need for absolute time recording.

The bit structure of the transmitted RF signal is known. The total duration of the transmitted data carrying RF signal should be short enough so that the MU movement is insignificant to the calculation of the true position. A translational error resulting from the MU movement must be taken into account when setting the measurement parameters such as NREP and data transmission rate.

The internal clocks of the TUs and MU need not to be synchronized at all. All one needs to know is that these clocks are counting during the entire tracking period at a more or less the same counting rate (though some fluctuations and offsets between these clocks are allowed, and as explained above do not affect the timing procedure).

Example of Triangulation Procedure Using Four TUs of Which No More than Three are Coplanar Let $(x_i, y_i, z_i)$ be the Cartesian coordinates describing the position of the TUs with respect to some fixed origin $(x_0, y_0, z_0)$. Let the location of the receivers in a MU be described by $(x_t, y_t, z_t)$ measured with respect to same fixed origin $(x_0, y_0, z_0)$. At any given instance, a simple mathematical algorithm (quadrangulation) describes the position of the MU with respect to the distance between the TUs to a target object in that moment. Mathematically, the location is given by the following equations:

$$x_t(x_1-x_2)+y_t(y_1-y_2)+z_t(z_1-z_2)=A1$$

$$x_t(x_1-x_3)+y_t(y_1-y_3)+z_t(z_1-z_3)=A2$$

$$x_t(x_1-x_4)+y_t(y_1-y_4)+z_t(z_1-z_4)=A3$$

where $(x_i, y_i, z_i)$ are the coordinates of the $i^{th}$ transmitting TU and where $$A_1=\tfrac{1}{2}(R_1^2-R_2^2)+\tfrac{1}{2}c^2(\Delta t_2^2-\Delta t_1^2)$$

$$A_2=\tfrac{1}{2}(R_1^2-R_3^2)+\tfrac{1}{2}c^2(\Delta t_3^2-\Delta t_1^2)$$

$$A_3=\tfrac{1}{2}(R_1^2-R_4^3)+\tfrac{1}{2}c^2(\Delta t_4^2-\Delta t_1^2)$$

where $R_i$ is the distances between the $i^{th}$ TU to the MU at that moment, c is the speed of the US signal (340 msec in air at S.T.P.) and $\Delta t_i$ is the true TOF of the transmitted US signal from the $i^{th}$ TU to the MU US receiver. The solution of this set of three independent equations is called 3D triangulation and is a well-known and practiced method in the field of RFID and GPS. Expressing the equations in a matrix formulation gives:

$$\begin{bmatrix} x_t \\ y_t \\ z_t \end{bmatrix} = \begin{bmatrix} x_1-x_2 & y_1-y_2 & z_1-z_2 \\ x_1-x_3 & y_1-y_3 & z_1-z_3 \\ x_1-x_4 & y_1-y_4 & z_1-z_4 \end{bmatrix}^{-1} \begin{bmatrix} A_1 \\ A_2 \\ A_3 \end{bmatrix}$$

from which the position of the MU can be derived at any moment, based on the a-priori known fixed positions of the 4 TUs and the instantaneous derivations of the distance of the two MU receivers to each TU. These distances are calculated based on $\Delta t_1$, $\Delta t_2$, $\Delta t_3$ and $\Delta t_4$, the TOF derivations. In order for these equations to converge, the four TUs must be positioned at four different locations in the (x,y) plane and their z-coordinates (heights) must be significantly different.

Example of US+RF TOF Measurements

Figure 7A:
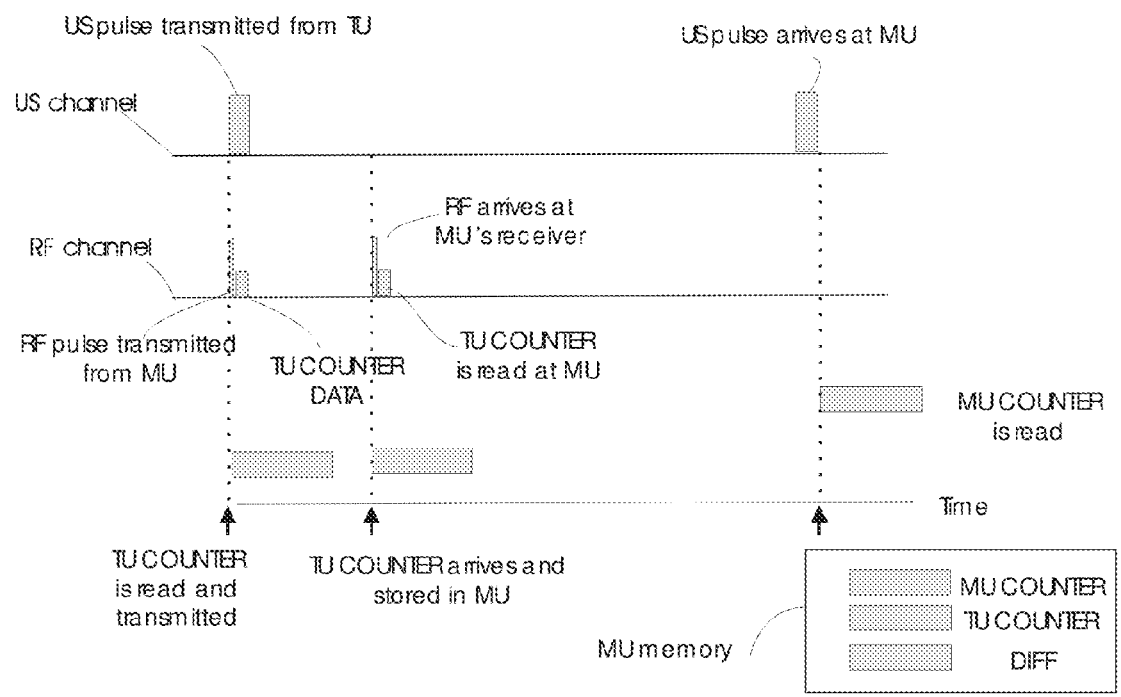
FIG. 7A shows transmission of US and RF with DATA and TU and MU CLOCK readings.

Assume an unknown fixed system delay $TAU_{TU}$ between the start of transmission of a TU RF signal and the moment of reading at the TU counter. This delay may be due to the electronics, and assumed always to be the same, at least during the few hours of operation of the system and under identical environmental conditions. Also, assume an unknown fixed system delay $TAU_{MU}$ between the actual arrival of the RF signal at the MU and the moment of reading of the MU counter. This delay is due to the electronics and RF wave shape, and, as $TAU_{TU}$, assumed to be constant. Let $CR_{TU}$ and $CR_{MU}$ be the fixed and known counting rates of, respectively, the TU and MU counters. Let $X_0$ be the known distance between the TU and the MU at a given time of calibration of the system. Further, assume that there is a random error $\delta_{error}$ introduced to the measurements because of electronics and environmental factors. Then:

$$X_0=c*[COUNTER_{TU}/CR_{TU}-COUNTER_{MU}/CR_{MU}+(TAU_{TU}-TAU_{MU})+\delta_{error}]$$

where $COUNTER_{TU}$ and $COUNTER_{MU}$ are the instantaneous counter readings at the TU and MU, respectively, upon time of transmission of the TU RF signal and upon time of arrival of the US signal at the MU and the moment of reading of the MU counter (see FIG. 7A). "c" represents the speed of RF signal propagation, Once the system is running, the true location of the MU becomes an unknown, denoted by X'. Then:

$$X'=X_0+c*[COUNTER'_{TU}-COUNTER_{TU})/CR_{TU}-[COUNTER'_{MU}-COUNTER_{MU})/CR_{TU}+\delta'_{error}+\delta_{error}],$$

where $COUNTER'_{TU}$ and $COUNTER'_{MU}$ are the new TU and MU counter readings. From these two equations one obtains:

$$X'=X_0+c*[(<COUNTER'_{TU}>NREP-COUNTER_{TU})/CR_{TU}-[(COUNTER'_{MU}-COUNTER_{MU})/CR_{TU}+<\delta_{error}>NREP].$$

Therefore, once the calibration readings $X_0$, $COUNTER_{TU}$ and $COUNTER_{MU}$ are read and known, the true position of the MU at any time can be calculated without the need to synchronize the system clocks and without a need to measure the fixed offset errors introduced to the measurements by internal and external causes. Also, because of the random nature of the stochastic error in each measurement, their summed contribution tends to average out. Therefore, under actual working conditions, the TU clock data is transmitted with a very large number of repetitions (NREP), and it is the average of this data train of clock readings that is received and read at the MU. With a large NREP and averaging, the errors in this TOF are reduced significantly, in proportion with the square root of NREP.

$$X'=X_0+c*[(<COUNTER'_{TU}>NREP-COUNTER_{TU})/CR_{TU}-[(COUNTER'_{MU}-COUNTER_{MU})/CR_{TU}+<\delta_{error}>NREP].$$

where <NREP> denotes an average over NREP repetitions.

One may assume that all clocks in the system have nearly the same count rate with a minute error due to jamming and drift. Preceding the clock data train sent from the TU to the MU is a preamble piece of data. This preamble contains necessary information such as identification of the transmitting TU, initialization of the receiver at the MU, length of data train, etc.

Figure 7B:
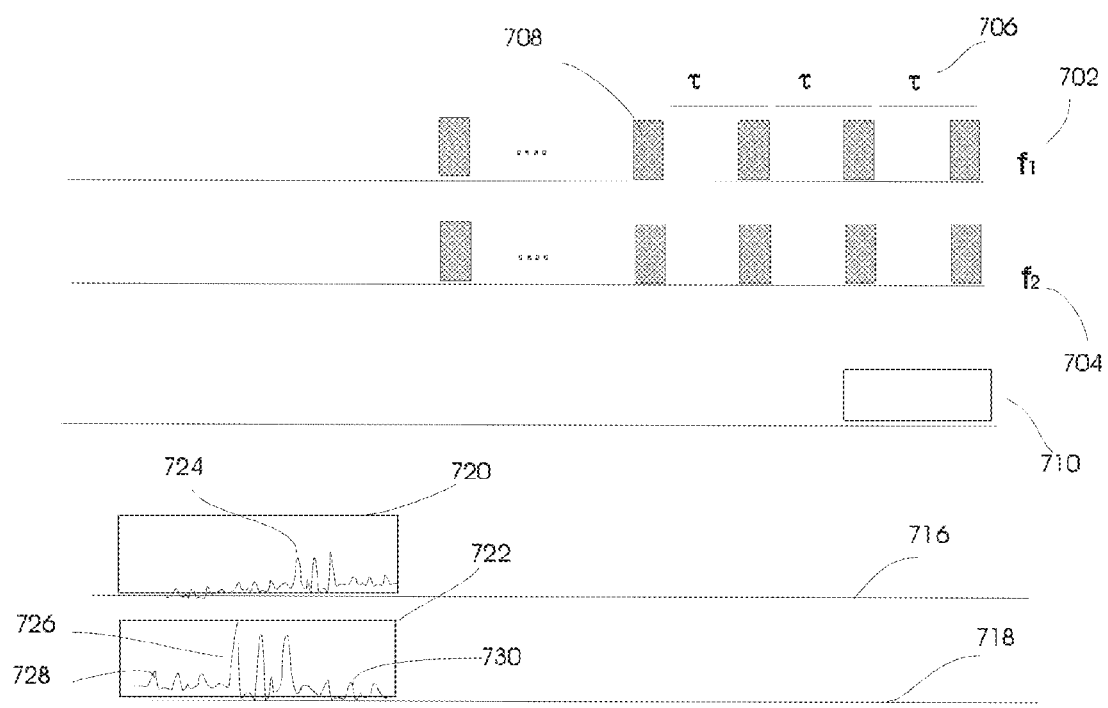
FIG. 7B shows a transmission sequence of US pulses with two different frequencies transmitted simultaneously and in parallel with RF data carrying pulse.
Figure 8A:
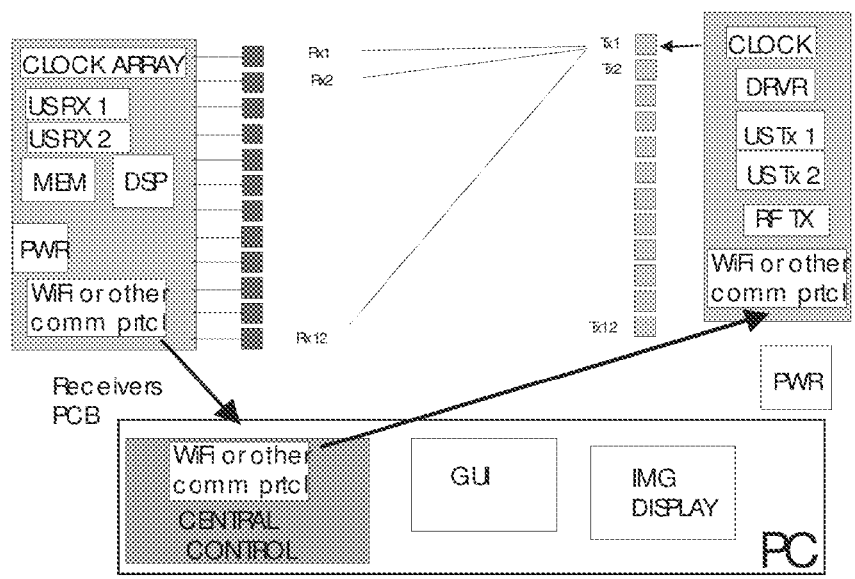
FIG. 8A shows schematically details of a TU and a MU with an array of receivers and an array of transmitters.
Figure 8B:
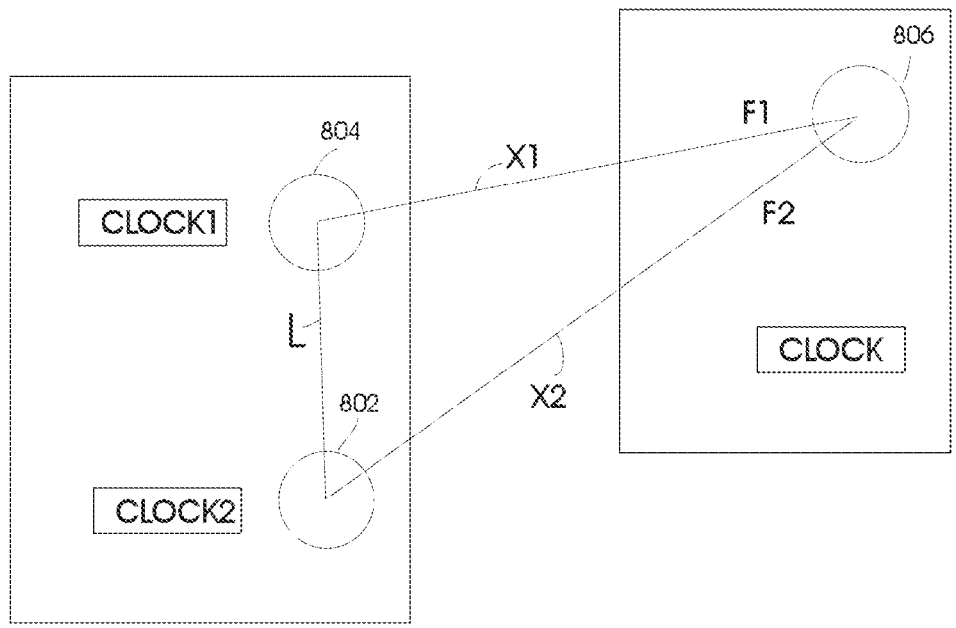
FIG. 8B shows schematically a MU with two US receivers of two separate frequencies, detecting signals from a TU having two separate US transmitters transmitting at two separate frequencies.
Figure 8C:
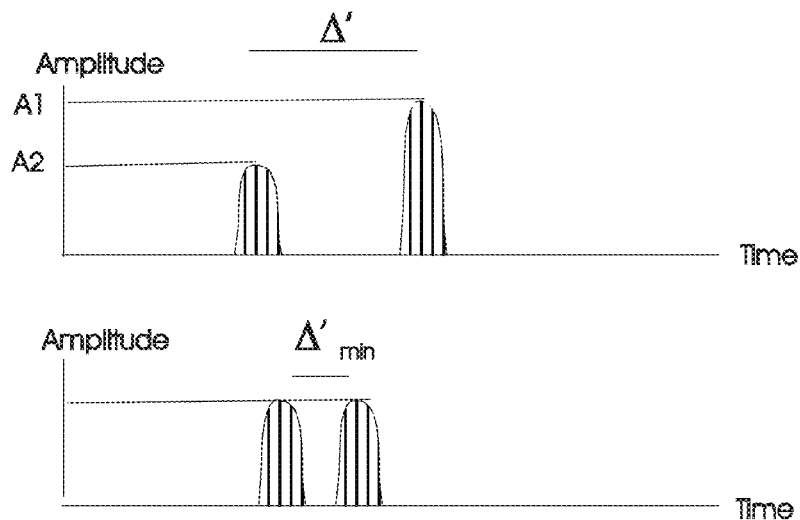
FIG. 8C shows amplitudes of detected signals with two frequencies f1 and f2 arriving at the two US receivers.
Figure 8D:
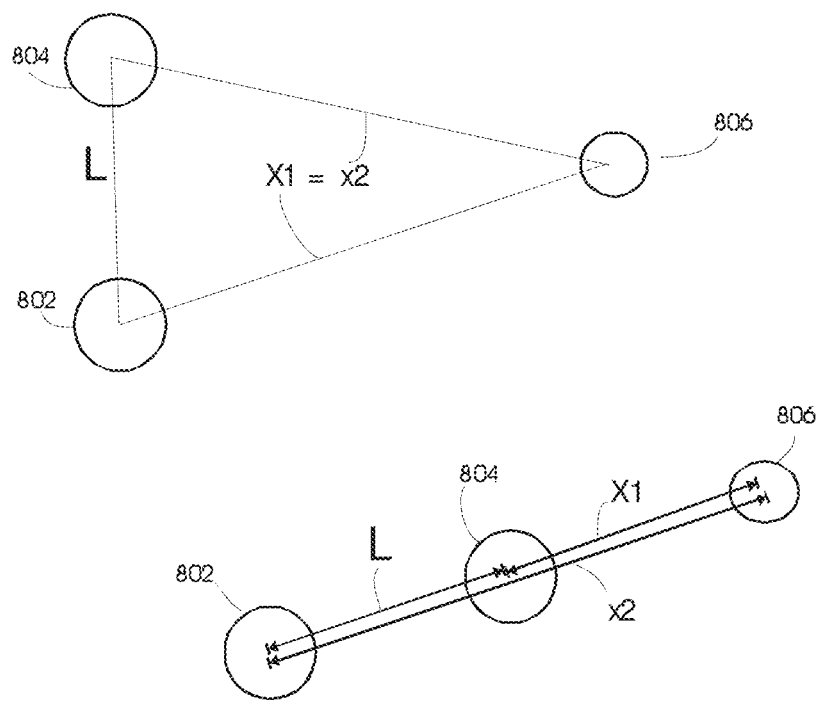
FIG. 8D shows the MU's inclination in space, once in the direction of a TU and once with both receivers equidistant from a TU.
Figure 8E:
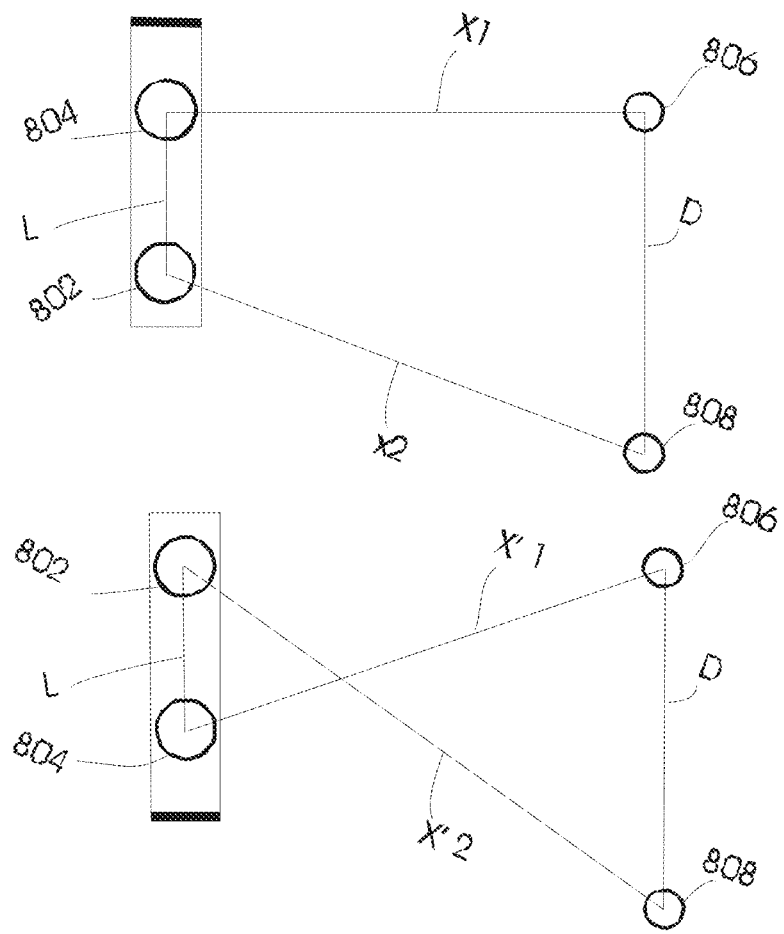
FIG. 8E shows two TU transmitters at different locations and two receivers at different locations, with separate frequencies f1 and f2.
Figure 8E:
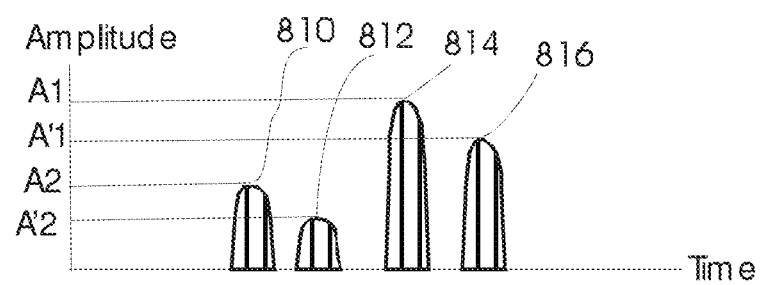

An Optional Clock Synchronization Procedure Without Physically Measuring Distance This procedure is described with reference to FIG. 7B and FIGS. 8A-D. FIG. 7B shows a transmission sequence of US pulses 708 with two different frequencies f1 and f2 transmitted simultaneously and in parallel with a RF data carrying pulse 710. The US pulses may be in a form of a pulse train 702 (for f1) or 704 (for f2) i.e. they may be repeated at given intervals τ 706 to improve detection and to remove ambiguities caused by reflections such as reflections 728, 730. The US pulses are sampled at the receiving MU by a digitizer and the peaks 724, 726 in the sampling window 720 are analyzed. Let the MU have two (first and second) receivers for respectively f1 and f2 separated by a distance L. Let there be two transmitters with frequencies f1 and f2 located together in a single TU. The transmitters and receivers are separated by respectively distances $X_1$ and $X_2$. FIG. 8 shows: (A) details of a TU and a MU with an array of receivers and an array of transmitters; (B) a MU with two US receivers of two separate frequencies, detecting signals from a TU with two separate US transmitters at two separate frequencies; (C) signals from two transmitters with two frequencies f1 and f2 arriving at the two US receivers. Both amplitudes and time separation can be measured and the distances $X_1$ and $X_2$ can be determined (D) a MU directed in space towards a TU such that its two receivers are equidistant from the TU ($X_1=X_2$); and (E) a most general procedure where MU receivers positions are inverted by rotation and four detected amplitudes are read.

Returning to FIG. 7B, assume a single clock CL (=COUNTER$_{TU}$) at a TU and two clocks $CL_1$ (=COUNTER$_{MU1}$) and $CL_2$ (=COUNTER$_{MU2}$) at the two receivers. Assume clocks $CL_1$ and $CL_2$ have similar count rates. CL is the reading of the transmitter clock sent at the time of transmission to the receiving unit as DATA. $CL_1$ is the reading at the receiver at the arrival time of the transmitted signal of frequency f1. $CL_2$ is the reading at the receiver at the arrival time of the transmitted signal of frequency f2. Based on the TOF of the pulses with f1 and f2, (ultrasound at speed c) one has:

$$DIFF_1=CL_1-X_1/c-CL$$

$$DIFF_2=CL_2-X_2/c-CL$$

where $DIFF_1$ and $DIFF_2$ are the true differences between the TU and receiver (MU) clock readings. In other words, these are synchronization offsets between the clocks. Since the clock count rates are assumed to be similar (in fact, the readings are done over the clock at the receiver) one may assume $DIFF_1=DIFF_2$ and thus:

$$CL_2-X_2/c-CL=CL_1-X_1/c-CL, \text{ or}$$

$$\Delta=CL_2-CL_1=(X_2-X_1)/c$$

except for internal deviation errors. As a matter of fact, $\Delta'=\Delta+\delta error$ where $\Delta'$ is the actual time difference with error. Because of the different distances, when positioned on the same time graph, one notices two peaks for the two signals $f_1$ and $f_2$ arriving at different times (see FIGS. 7B and 8C. If the two receivers are positioned equidistantly from the transmitter ($X_1=X_2$), the two peaks become one ($\Delta=0$) except for an internal deviation $\delta_{error}$ In such a case $\Delta'_{min}=\delta_{error}$ and is obtained by reading of the difference between the two peaks. When the two receivers (spaced L apart) are positioned linearly with the transmitter (with the first receiver closer to the transmitter), FIG. 8D, the two peaks are at a maximal separation $$\Delta'_{max}=L/c+\delta_{error}=L/c+\Delta'_{min}.$$

Both $\Delta'_{max}$ and $\Delta'_{min}$ are measurable. Assuming that the signal amplitude is inversely proportional to the distance of propagation, then the received signal amplitude is given by A=k/x. where "x" is distance in any direction. For other propagation patterns, a decrease in signal amplitude will be generally given by $A=k/x^\alpha$, where α is a parameter related to absorption or dissipation mechanisms α≠1. Thus, $A_2/A_1=x_1/x_2$ and together with $CL_2-CL_1=(X_2-X_1)/c$, one obtains:

$$X_1=c(CL_1-CL_2)+X_2$$

$$X_1=(A_2/A_1)X_2$$

where $A_1$ and $A_2$ are the measured amplitudes of the two peaks of $f_1$ and $f_2$ respectively (obviously $A_1>A_2$ as receiver 1 is closer to the transmitter). Therefore:

$$X_1=A_2/(A_2-A_1)c(CL_1-CL_2)$$

This means that $X_1$ can be derived by measuring the amplitudes ratio and the clock's difference. One need not, for purpose of initial synchronization, physically measure the distance from the receivers to a transmitter. Once $X_1$ is derived, the synchronization difference $DIFF_1$ between transmitter clock and receiver clock can be derived from $DIFF_1=CL_1-X_1/c-CL$.

This method can be further extended (FIG. 8E) to the case in which two transmitters 806. 808 separated by a distance D and transmitting at two frequencies f1 and f2 to two receivers 802, 804 in a MU are enough to read distances $X_1$ and $X_2$ without a need for initial calibration. The receivers are separated by a distance L. Assuming that the signal decays in proportion to the distance of propagation, one will read a signal $S_1=k_1/X_1$ at receiver 804 and a signal $S_2=k_2/X_2$ at receiver 802, with $k_1$ and $k_2$ being unknown proportionality constants (transmitter electronics and frequency dependent). The MU may be positioned with the two receivers aligned parallel to the two TUs 806 and 808 such that in a first position, receiver 804 is closer to TU 806, and in a second position receiver 802 is closer to TU 806. This provides separate signal readings $S_1$ (810), $S_2$ (812) for the first position and $S'_1$ (814) and $S'_2$ (816) for the second position. The signals have respective amplitudes $A_1$ (814), $A'_1$ (816), $A_2$ (810) and $A'_2$ (812). The signal amplitudes are compared and the distances are derived from the amplitudes. Since $X_1/X'_1=A'_1/A_1$ and $X_2/X'_2=A'_2/A_2$ and since the geometry allows to express X1 and X2 in terms of $X'_1$, $X'_2$, D and L, one has 4 equations with 4 unknowns $X_1$, $X_2$, $X'_1$ and $X'_2$ and the solution is straightforward. The procedure above assumes that the MU is parallel to the two transmitters, although other arbitrary angles can be assumed.

One-to-One Mapping of Image Space to Real Space

This mapping is described with reference to FIG. 4. At least three markers M1, M2 and M3 marked with vectors $m_1$, $m_2$ and $m_3$ respectively are attached to body (organ) when the body is in "image space" coordinate system XYZ. A point P in the image space is marked with vector p. If the body is assumed to be rigid, when it is moved to a different location with a different, "real space" coordinate system X'Y'Z', the relative positions of vectors and points in it remain unchanged. This implies:

$$\vec{m}_i \cdot \vec{p} = \vec{m}'_i \cdot \vec{p}' \text{ for } i=1,2,3$$

The only unknown here is $\vec{p'^z}$ the position vector of point P real space coordinate system X'Y'Z The solution is:

$$\begin{pmatrix} p'_x \\ p'_y \\ p'_z \end{pmatrix} = \begin{bmatrix} m'_{1x} & m'_{1y} & m'_{1z} \\ m'_{2x} & m'_{2x} & m'_{2x} \\ m'_{3x} & m'_{3x} & m'_{3x} \end{bmatrix}^{-1} \begin{pmatrix} \vec{m}_1 \cdot \vec{p} \\ \vec{m}_2 \cdot \vec{p} \\ \vec{m}_3 \cdot \vec{p} \end{pmatrix}$$

where $\vec{p} = (p_x, p_y, p_z)$ are the measured coordinates of point P in the image space (with respect to the scanner's fixed iso-center as origin of coordinate system), $\vec{m}_1 = (m_{1x}, m_{1y}, m_{1z})$, $\vec{m}_2 = (m_{2x}, m_{2y}, m_{2z})$ and $\vec{m}_z = (m_{3x}, m_{3y}, m_{3z})$ are the measured coordinates of markers $M_1$, $M_2$ and $M_3$ respectively, in same image space, and $\vec{m'}_z = (m'_{1x}, m'_{1y}, m'_{1z})$, $\vec{m'}_2 = (m'_{2x}, m'_{2y}, m'_{2z})$ and $\vec{m'}_z = (m'_{3x}, m'_{3y}, m'_{3z})$ are the measured coordinates of markers $M'_1$, $M'_2$ and $M'_3$ respectively, in real space, being read by the tool (with respect to operating room's fixed origin).

Improving Tool Positioning Accuracy by Accounting for Tissue Elastic Properties

Figure 9:
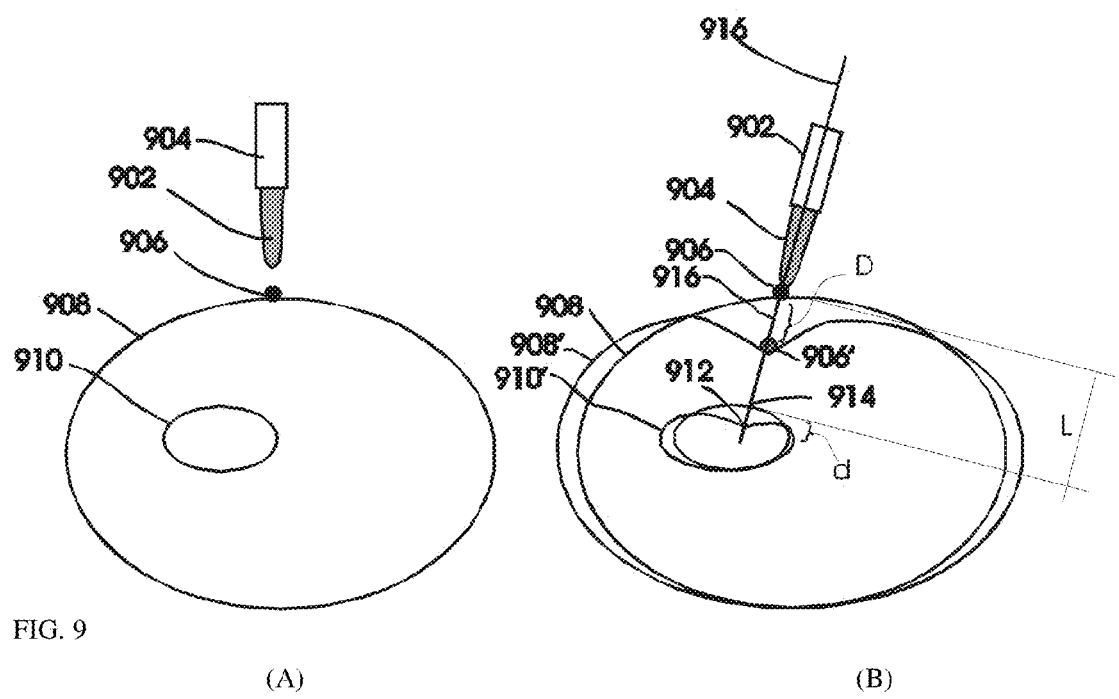
FIG. 9 shows tool positioning adjustments that may be made by the operator to account for tissue flexibility under pressure.

FIG. 9 shows tool positioning adjustments that may be made by the operator to account for tissue flexibility under pressure. The figure shows in (A) a tool 902 attached to a MU 904, the tool close to touching a body 908 that includes an organ 910. A marker 906 on the body is also shown. During or after the marker's position registration procedure, the operator may press marker 906 (as well as all other markers) with the tool tip, to compress the body tissue along a propagation pressure line (axis) 916. Under pressure, the body and the organ change shapes to respectively shapes 908' and 910'. The marker moves to a pressed marker position 906'. The compression is done to a maximum compression distance (displacement) D that the operator feels is allowed without causing pain or damage. A point on the organ along axis 916 changes position from an un-pressed position 914 to a final pressed position 912. By pressing of a button (not shown) the operator then registers the marker's maximal displacement under pressure against the body's flexible texture. By doing so over at least three markers, an elasticity displacement map can be constructed using a known mathematical algorithm. Basically, it is assumed that an internal displacement d is directly proportional to D and inversely proportional to the initial distance between the marker and the internal organ L, i.e. d=cD/L where e is the elasticity of the intermediate tissue between the marker and the internal organ. This allows corrections in real time for the displacement of patient's organs under the pressure of the interventional tool during the interventional procedure. Corrections to reconstructed images obtained from the pre-scanned 3D data volume can be done accordingly and thus overcome inaccuracies expected due to non-rigidity of tissues under tool pressure during operation.

While this disclosure has been described in terms of certain embodiments and generally associated methods, alterations and permutations of the embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

All patent applications and publications mentioned in this specification are herein incorporated in their entirety by reference into the specification, to the same extent as if each individual patent application or publication was specifically and individually indicated to be incorporated herein by reference. In addition, citation or identification of any reference in this application shall not be construed as an admission that such reference is available as prior art.

What is claimed is:

1. A system for stereotactic positioning in real time of a first object or part thereof relative to a second object or part thereof, the system comprising:
   a. at least three transmitting units (TUs) arranged spatially such that no more than three TUs are coplanar, each TU comprising at least one ultrasound (US) transmitter, at least one radio frequency (RF) transmitter and at least one TU clock, wherein at least one TU includes two US transmitters configured to transmit on two different frequencies, respectively;
   b. a mobile unit (MU) fixedly coupled to the first object, the MU comprising at least one MU clock, at least one RF transmitter/receiver and at least two US receivers spaced apart and positioned in a predetermined geometrical relation relative to the first object or part thereof and to one another;
   c. at least one storage unit for storing scanned images of the second object; and
   d. a central processing unit (CPU) configured to:
      (1) receive data from the US and RF receivers from said MU;
      (2) receive imaging data from said storage unit, said imaging data comprising at least one scanned image of the second object with at least three image markers indicated over the at least one image of the second object;
      (3) identify positions of at least three real markers over the second object in real space;
      (4) determine a real space position and inclination of said first object or part thereof based on time-of-flight (TOF) data obtained from combined US transmissions between said US transmitters of the TUs and said US receivers at the MU and RF transmissions between said RF transmitters in said TUs and said RF receiver in said MU using said TUs and MU clocks;
      (5) determine real space positioning and inclination of the first object or part thereof relative to real space location of the second object or part thereof, based on locations of the at least three real markers in real space and the at least three image markers in the imaging data;
      (6) reconstruct, in real time, an image of the second object or part thereof with an indication of the first object or part thereof based on real time and real space positioning and inclination of the first object or part thereof in respect to the position of the second object or part thereof; and
      (7) display said reconstructed image.

2. The system of claim 1, wherein the first object is an interventional tool.

3. The system of claim 2, wherein the second object is an organ and said CPU is further configured to reconstruct image space data including first and second reconstructed slices of the organ, wherein the first slice is a target slice through a target lesion in the organ, wherein the second slice is a current slice through a current position of the interventional tool or a tip part thereof and wherein both slices are orthogonal to a tool length axis passing through the tip.

4. The system of claim 3, wherein said CPU is further configured to reconstruct image space data further including a third, sagittal slice, sagittal to a virtual axis drawn between the tip and the target lesion.

5. The system of claim 1, wherein each TU is configured to transmit time-stamp data through RF data transmission thereof, and wherein the CPU is further configured to determine the TOF after synchronization of the respective TU and MU clocks using RF time-stamp data transmissions.

6. The system of claim 1, wherein said MU comprises a local processing unit configured to process signals and associated data to distinguish between different signals and time-stamp data.

7. The system according to claim 1, wherein said at least two US receivers at the MU comprises at least two US receivers configured for receiving US signals of the different frequencies.

8. A method for stereotactic positioning in real time of a first object or part thereof relative to a second object or part thereof, the method comprising:
   a. providing at least three transmitting units (TUs) arranged spatially such that no more than three of the TUs are coplanar, each TU comprising at least one ultrasound (US) transmitter, at least one radio frequency (RF) transmitter capable of transmitting time-stamp data and at least one TU clock, wherein at least one TU includes two US transmitters configured to transmit on two different frequencies, respectively;
   b. providing a mobile unit (MU) fixedly coupled to the first object, the MU including at least one MU clock, at least one RF transmitter/receiver and at least two US receivers spaced apart and positioned in a predetermined geometrical relation relative to the first object or part thereof and to each other;
   c. receiving data from the US and RF receivers from said MU;
   d. receiving imaging data comprising at least one image of the second object with at least three image markers indicated over the at least one image of the second object;
   e. identifying positions of at least three real markers over the second object in real space;
   f. determining a real space position and inclination of said first object or part thereof based on time-of-flight (TOF) data obtained from combined US and RF transmissions between said US transmitters of the TUs and said US receivers at the MU and between said RF transmitter at the TU and said RF receiver in said MU using said TU and MU clocks;
   g. determining real space positioning and inclination of the first object or part thereof relative to real space location of the second object or part thereof, based on locations of the at least three real markers in real space and the at least three image markers in the imaging data;
   h. reconstructing, in real time, an image of the second object or part thereof with an indication of the first object or part thereof based on real time and real space positioning and inclination of the first object or part thereof in respect to the position of the second object or part thereof; and
   i. displaying said reconstructed image.

9. The method of claim 8, wherein the step of obtaining of TOF data from combined RF and US transmissions includes transmitting simultaneously from each TU RF time-stamp data and a US pulse without synchronizing the respective TU clock with the MU clock, and reading the difference between each TU clock and the MU clock, thereby determining a particular TOF reading between the respective TU and the MU.

10. The method of claim 8, wherein the step of obtaining of TOF data from combined RF and US transmissions includes interleaving RF signal transmissions with the RF time-stamp data transmissions, wherein a RF signal is generated in the respective TU, transmitted simultaneously with a US pulse to the MU and used to start the MU receiver clock, and wherein a later arrival and detection at the MU of the US pulse stops the MU clock, thereby determining a particular TOF reading between the respective TU and the MU.

11. The method of claim 8, wherein the second object is a patient's organ and the method further comprising fixedly attaching the at least three real markers to the patient, touching each real marker with a tip of the first object relative location of which is known in respect to location of the US receivers, while the real markers are in the real space, and recording real space coordinates of each real marker to assist in location and mapping of the organ from the image space to the real space using the locations of the image markers to locate the organ.

12. The method of claim 8, further comprising the step of synchronizing each TU clock with the MU clock prior to said determining a real space position of the first object or part thereof.

13. The method of claim 12, wherein said synchronizing comprises synchronizing without measuring distances between the clocks by measuring amplitudes of US pulses transmitted from a respective TU to the MU while the MU receivers are in a first position and in a second position and using amplitudes of the US pulses to synchronize the respective TU clock with the MU clock.

14. A system for spatial positioning in real time of a first object or part thereof, said system comprising:
   a. at least three transmitting units (TUs) arranged spatially such that no more than three of the TUs are coplanar, each TU comprising at least one ultrasound (US) transmitter, at least one radio frequency (RF) transmitter and at least one TU clock, wherein at least one TU includes two US transmitters configured to transmit on two different frequencies, respectively;
   b. a mobile unit (MU) fixedly coupled to the first object, the MU comprising at least one MU clock, at least one RF transmitter/receiver and at least two US receivers spaced apart and positioned in a predetermined geometrical relation relative to the first object or part thereof and to one another; and
   c. a central processing unit (CPU) configured to: receive data via a wireless communication transmitter from said MU indicative of received US signal data and of data outputted from the TUs and MU clocks and determine a real space position and inclination of said first object or part thereof based on US time-of-flight (TOF) data obtained from the received data,
   wherein said position and inclination of the first object or part thereof is determined using an algorithm based on triangulation.

15. The system according to claim 14, wherein the CPU is further configured to obtain TOF data from combined RF and US transmissions, which includes transmitting simultaneously from each TU RF time-stamp data and a US pulse, and determining the difference between each TU clock and the MU clock, said TOF data being calculated using said difference.

16. The system according to claim 14, wherein said CPU is further configured to receive imaging data of a second object, said imaging data including image markers indicated on said second object, and to present real space and real time position of the first object or part thereof in relation to position of the second object or part thereof using the image markers indicated in the imaging data and real markers positioned in corresponding locations in respect to the second object.

17. A method for spatial positioning in real time of a first object or part thereof, said method comprising:
  i. providing at least three transmitting units (TUs) arranged spatially such that no more than three of the TUs are coplanar, each TU comprising at least one ultrasound (US) transmitter and at least one radio frequency (RF) transmitter, wherein at least one TU includes two US transmitters configured to transmit on two different frequencies, respectively;
  ii. providing a mobile unit (MU) fixedly coupled to the first object, the MU comprising at least one MU clock, at least one RF transmitter/receiver and at least two US receivers spaced apart and positioned in a predetermined geometrical relation relative to the first object or part thereof and to one another; and
  iii. receiving data from the US and RF receivers from said MU; and
  iv. determining a real space position and inclination of said first object or part thereof based on time-of-flight (TOF) data obtained from combined US transmissions between said US transmitters of the TUs and said US receivers at the MU and RF transmissions between said RF transmitters in said TUs and said RF receiver in said MU, using also data from the MU and TU clocks,
  wherein said position and inclination of the first object or part thereof is determined using an algorithm based on triangulation.

18. The method according to claim 17 further comprising using said real time position and inclination of the first object determined by a processing unit for real time reconstruction of imaging data of a second object, for indicating real space and real time position of the first object or part thereof in relation to position of the second object or part thereof using image markers in the imaging data and real markers positioned in corresponding locations in respect to the second object.

* * * * *